US00PP21566P3

(12) United States Plant Patent
Pinochet

(10) Patent No.: US PP21,566 P3
(45) Date of Patent: Dec. 14, 2010

(54) VARIETY OF PEACH-ALMOND TREE NAMED 'NANOPAC'

(50) Latin Name: [*(Prunus dulcis×P. persica)×(P. dulcis×P. persica)*]
Varietal Denomination: Nanopac

(75) Inventor: Jorge Pinochet, Barcelona (ES)

(73) Assignee: Agromillora Iberia, S.L., Barcelona (ES)

( * ) Notice: Subject to any disclaimer, the term of this patent is extended or adjusted under 35 U.S.C. 154(b) by 0 days.

(21) Appl. No.: 12/454,304

(22) Filed: May 15, 2009

(65) Prior Publication Data

US 2010/0293676 P1 Nov. 18, 2010

(51) Int. Cl.
*A01H 5/00* (2006.01)

(52) U.S. Cl. ..... Plt./180

(58) Field of Classification Search ..... Plt./180, Plt./155

See application file for complete search history.

*Primary Examiner*—Kent L Bell
(74) *Attorney, Agent, or Firm*—The Webb Law Firm

(57) ABSTRACT

A new and distinct hybrid peach-almond tree used as a rootstock that exhibits root-knot nematode resistance and compatibility with peach, nectarine, almond, and plum varieties.

3 Drawing Sheets

Botanical classification: [(*Prunus dulcis×P. persica*)×(*P. dulcis×P. persica*)].

Varietal denomination: 'Nanopac'.

BACKGROUND OF THE INVENTION

The present invention comprises a new and distinct cultivar of peach-almond hybrid [(*Prunus dulcis×P. persica*)×(*P. dulcis×P. persica*)] used as a rootstock known by the varietal name 'Nanopac'. The new variety was discovered in Barcelona, Spain in 2000 as a result of a planned breeding program. The new variety is the result of a cross between 'Felinem' (*Prunus dulcis×P. persica*) (female parent, unpatented) and an unnamed plant from the cross of 'Marcona'×'Nemaguard' (male parent, unpatented). The purpose of the breeding program was to develop rootstocks that are adaptive to Mediterranean conditions, with low to medium vigor, low chilling requirements, a tolerance to calcareous soils, and good productivity. The new variety exhibits similar good tolerance to calcareous soils, moderate root-knot nematode resistance, and low chilling requirements to both parents, but differs from both parents in its almond-like leaves, medium vigor, and the fact that it tolerates waterlogging conditions better. Further, the new variety has similar green leaves, productivity and root-knot nematode resistance to 'Nemaguard' (unpatented), but differs from 'Nemaguard' in its almond-like leaves, medium vigor, and tolerance to iron chlorosis. The new variety has been trial and field tested and has been found to retain its distinctive characteristics and remain true to type through successive propagations. The following characteristics distinguish 'Nanopac' from other varieties known to the breeder:

1. Medium vigor with a small trunk cross-section area;
2. Almond-like leaves;
3. No suckering;
4. Better tolerance to alkaline soils and salinity than most peach rootstocks;
5. Moderate resistance to root-knot nematodes (*Meloidogyne* spp.);

6. Induces early fruit maturation in peach varieties; and
7. Low chilling requirements.

DESCRIPTION OF THE DRAWINGS

The accompanying photographic drawings illustrate the new variety with the color being as nearly true as is possible with color illustrations of this type.

DESCRIPTION OF THE PLANT

Figure 1:
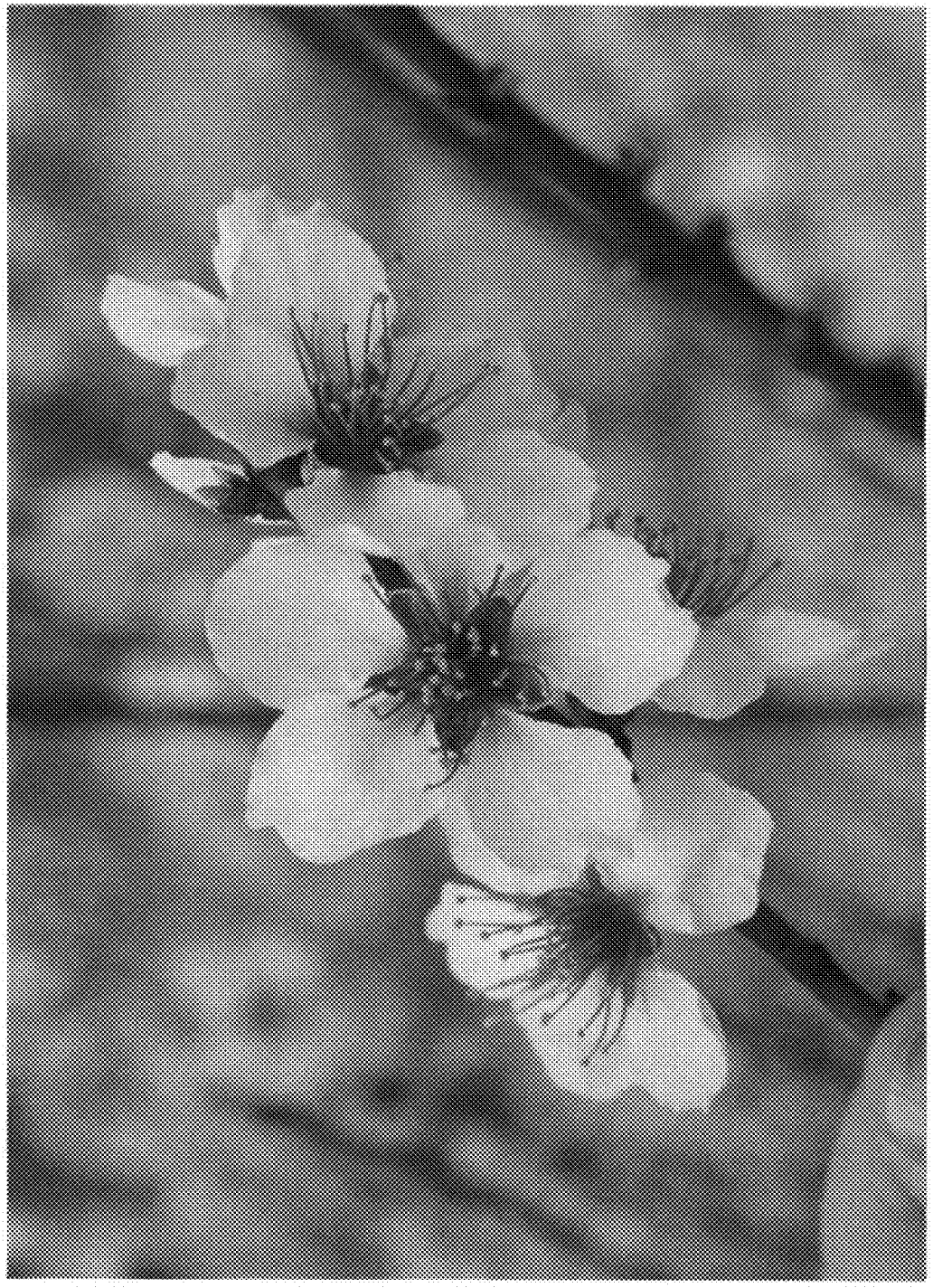
FIG. 1 shows the flowers of the new variety.
Figure 2:
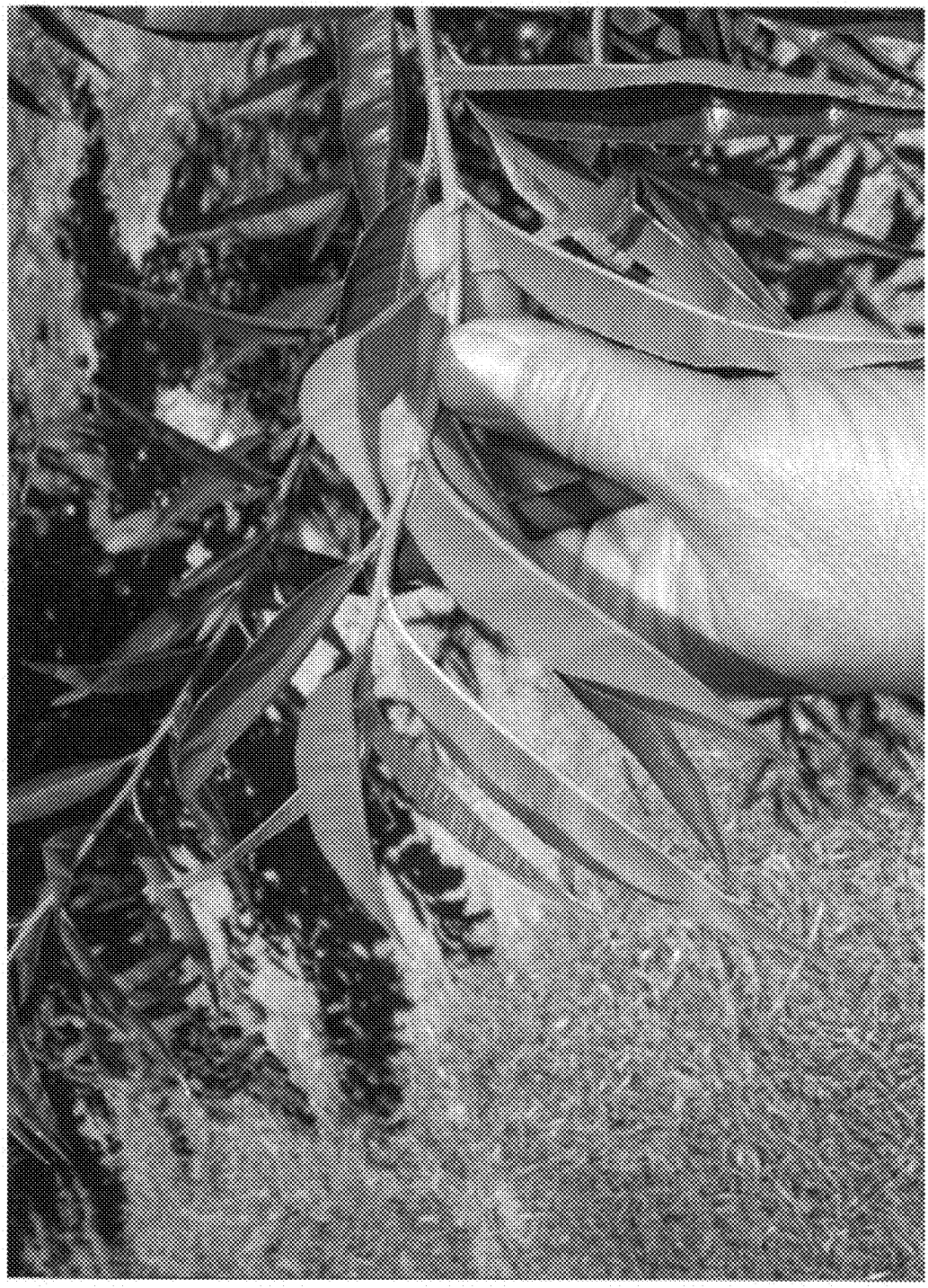
FIG. 2 shows the leaves of the new variety.
Figure 3:
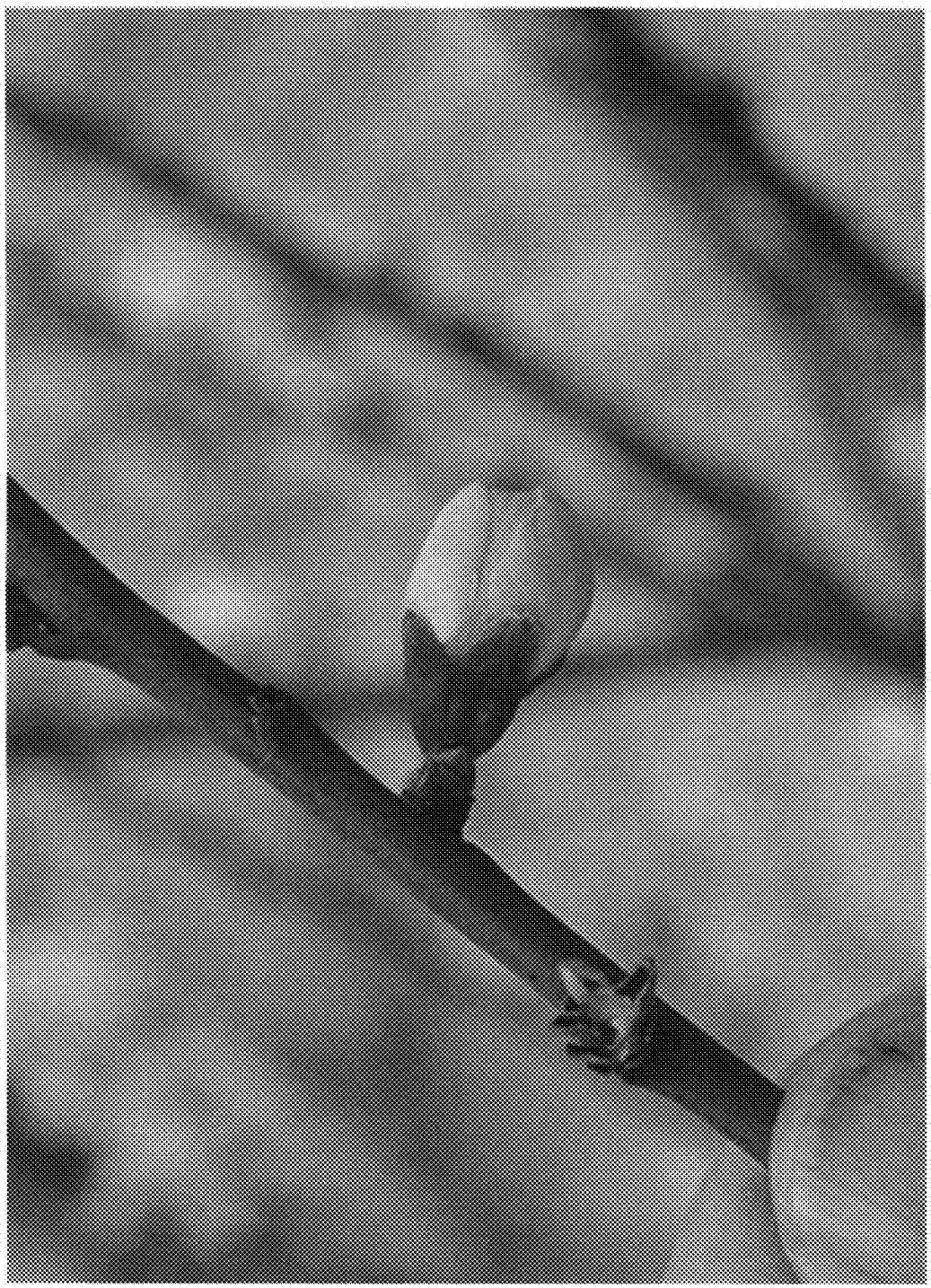
FIG. 3 is a close-up view of a bud of the new variety.

The following detailed description sets forth the characteristics of the new cultivar. The data which defines these characteristics was collected under natural daylight on plants produced by asexual reproductions via in vitro propagation carried out in Barcelona, Spain. The plants were grown under normal field conditions with drip irrigation in 5 and 40 liter containers. Color designations are presented with reference to the "Dictionary of Color" by A. Maerz and M. Rea Paul, Second Edition (1950).

TREE

Age: 8 years.
Size: 2.7 meters tall.
Vigor: Medium.
Density: Low.
Form: Compact.
Production: Abundant.
Growth type: Upright.
Bearing: Non-fruit bearing.
Pathogen resistance:
*Fungal disease.*—Oidium.
*Insects.*—Unknown.
*Mites.*—Unknown.
*Viruses.*—Unknown.

*Other diseases.*—Root-knot nematodes (*Meloidogyne* spp.).

Rootstock performance:

*Root sprouts* (*suckering*).—Not present.

*Anchorage.*—Good with a big, fibrous root system.

*Compatibility.*—Compatible with peach, nectarine, almond, and plum varieties.

*Vigor.*—Medium (20-25% less than 'Nemaguard').

Trunk:

*Size.*—Reduced trunk cross-sectional area; variable from 13 to 15 cm. in diameter.

*Surface texture.*—Smooth with horizontal lenticels.

*Bark color.*—Plate 6, A 7.

*Lenticels.*—Length: 3 to 5 mm. Width: 1 to 1.5 mm. Color: Plate 53, A 1 (Gull). Density: Highly abundant.

Branches:

*Diameter.*—Variable; from 0.5 to 2 cm. in the same season.

*Surface texture.*—Smooth in the current season with minor scarfskin as maturity advances.

*Color.*—Plate 14, A 3 (Sandy Beige).

*Form.*—Circular in diameter.

*Average angle.*—Acute.

*Bud arrangement.*—Helicoidal throughout the branch.

*Lenticels.*—Length: 2 to 4 mm. after the second year of growth. Width: 0.5 to 1 mm. Shape: Elongated horizontally. Density: Medium to high as maturity advances. Color: Plate 46, A 1 (Cemetery Natural Grey).

Leaves:

*Length.*—10 to 12 cm.

*Width.*—2.5 to 3 cm.

*Form.*—Lanceolate.

*Texture.*—Smooth.

*Thickness.*—Medium.

*Base.*—Acute.

*Apex.*—Acute.

*Margin.*—Crenate.

*Pubescence.*—Upper surface: Absent. Lower surface: Absent.

*Color.*—Young leaves: Upper surface: Plate 21, L 7. Lower surface: Plate 20, I 6. Mature leaves: Upper surface: Plate 22, K 7 (Spinach Green). Lower surface: Plate 21, H 6.

*Petiole.*—Shape: Straight with a central groove along the upper side with 1 or 2 very small sized nectaries near the base of the leaf. Length: 7 to 10 mm. Diameter: 1 to 1.5 mm. Color: Plate 20, J 3 (Shadow Green).

*Veins.*—Venation type: Tree type disposition. Color: Upper surface: Plate 20, L 3 (Certosa). Lower surface: Plate 20, H 1.

Flower buds:

*Pedicel.*—Length: 1 to 2 mm. Diameter: 0.5 to 1 mm. Color: Plate 39, A 2 (Jack Rabbit).

*Bud.*—Length: 8 to 10 mm. Width: 6 to 8 mm. Shape: Ovoid. Color: Plate 53, B 2 (Mist).

Flowers:

*Bloom timing.*—February 20th in Barcelona, Spain.

*Blooming period.*—10 to 15 days.

*Pollination requirements.*—None.

*Number of flowers per raceme.*—Normally individual, occasionally 2 present.

*Fragrance.*—Low in strength and rose-like.

*Petals.*—Number: 5. Length: 12 to 16 mm. Width: 12 to 14 mm. Shape: Rounded. Aspect: Cupped upwards and inwards. Margin: Undulate. Texture and appearance: Smooth.

*Color.*—When opening: Upper surface: Plate 50, A 1. Lower surface: Plate 50, B 1. Fully opened: Upper surface: Plate 49, B 1. Lower surface: Plate 49, B 1.

*Sepals.*—Shape: Elliptic. Margin: Smooth. Texture: Pubescent. Length: 9 to 10 mm. Width: 4 to 5 mm. Color: Upper surface: Plate 54, J 6 (Rhododendron). Lower surface: Plate 55, E 2 (Mauve Castor).

*Stamens.*—Number (per flower): 25 to 30. Filament length: 11 to 14 mm.

*Anthers.*—Shape: Kidney-shaped. Length: 1 to 1.3 mm. Color: Plate 13, E 4 (Sudan).

*Pollen.*—Color: Plate 12, J 5 (Lightstone). Amount: Abundant.

*Pistils.*—Length: 11 to 13 mm.

*Style.*—Length: 9 to 10 mm. Color: Plate 5, J 6 (Harvard Crimson Jockey).

*Stigma.*—Shape: Rounded. Color: Plate 14, G 4 (Hemp).

Fruit description: No fruit produced to date.

Use: As a rootstock for peach, nectarine, and almond varieties.

Winter hardiness: Hardy (under the conditions in Spain).

Bud winter hardiness: Medium.

Drought tolerance: Moderately tolerant.

I claim:

1. A new and distinct variety of hybrid peach-almond tree, as illustrated and described herein.

* * * * *